(12) United States Patent
Giles et al.

(10) Patent No.: US 8,759,397 B2
(45) Date of Patent: Jun. 24, 2014

(54) DETERGENT COMPOSITION

(75) Inventors: Matthew Robert Giles, Hoole (GB);
Nicholas John Dixon, Upton (GB)

(73) Assignee: Innospec Limited (GB)

( * ) Notice: Subject to any disclaimer, the term of this patent is extended or adjusted under 35 U.S.C. 154(b) by 435 days.

(21) Appl. No.: 12/664,714

(22) PCT Filed: Jul. 21, 2008

(86) PCT No.: PCT/GB2008/050602
§ 371 (c)(1),
(2), (4) Date: Jan. 15, 2010

(87) PCT Pub. No.: WO2009/013534
PCT Pub. Date: Jan. 29, 2009

(65) Prior Publication Data
US 2010/0183533 A1 Jul. 22, 2010

(30) Foreign Application Priority Data
Jul. 26, 2007 (GB) .................................. 0714575.8

(51) Int. Cl.
*A61K 31/197* (2006.01)
(52) U.S. Cl.
USPC .......................................... 514/566; 562/565
(58) Field of Classification Search
CPC ..................................................... A61K 8/44
See application file for complete search history.

(56) References Cited

U.S. PATENT DOCUMENTS

| 4,704,233 A | 11/1987 | Hartman et al. |
| 5,780,419 A | 7/1998 | Doumen et al. |
| 2010/0191012 A1 | 7/2010 | Giles et al. |

FOREIGN PATENT DOCUMENTS

| EP | 0713910 A2 | 10/1995 |
| EP | 0771864 A | 5/1997 |
| GB | 2294694 A | 11/1994 |
| GB | 2283494 A | 5/1995 |
| WO | 94/03553 A1 | 2/1994 |
| WO | 9702010 A | 6/1996 |
| WO | 9730209 A | 8/1997 |

OTHER PUBLICATIONS

Kovaleva et al, Zhurnal Neorganiskoi Khimii, Magnesium and Calcium Ethylenediamine-disuccinates, 1991, 36(3), pp. 664-669, English translation.*
Rämö, Department of Process and Environmental Engineering, University of Oulu, Hydrogen Peroxide-Metal-Chelating Agents; Interactions and Analytical Techniques, 2003, pp. 1-52, recovered from internet at http://herkules.oulu.fi/isbn9514269756/ on Apr. 30, 2013.*
Database CA [Online] Chemical Abstracts Service, Columbus, Ohio, US; retrieved from STN Database accession No. 1991:440744.
Kovaleva, I.B. et al. "Magnesium and calcium ethylenediaminedisuccinates." Zhurnal Neorganicheskoi Khimii 36(3), 664-9 Coden: ZNOKAQ; ISSN: 0044-457X, 1991.
Witschel, M. et al. Purification and Characterization of a Lyase from the EDTA-degrading bacterial strain DSM 9103 that catalyzes the splitting of [S,S]-ethylenediaminedisuccinate, a structural isomer of EDTA. Biodegradation, Kluwer Academic Publishers, NL, vol. 8(6), Jan. 1, 1998, 419-428.
International Search Report dated Oct. 14, 2008 for PCT/GB08/050602.
Search Report under Section 17 dated Nov. 28, 2007 for GB0714575.8.
International Preliminary Report on Patentability, and Written Opinion of the International Searching Authority, dated Jan. 26, 2010 from parent international patent application GB/2008/050602, filed on Jul. 21, 2008, which in turn claims priority to Great Britain Patent Application No. 0714575.8, filed on Jul. 26, 2007.
Tandy et al., "Extraction of Heavy Metals from Soils Using Biodegradable Chelating Agents," Environ. Sci. Technol. 2004, vol. 38, pp. 937-944.
First Office Action issued by the State Intellectual Property Office, P.R. China, dated Apr. 20, 2012 for Chinese Patent Application U.S. Appl. No. 200880100499.6.

* cited by examiner

*Primary Examiner* — Paul A Zucker
(74) *Attorney, Agent, or Firm* — Burns & Levinson, LLP; Janine M. Susan

(57) ABSTRACT

The present invention provides a salt of ethylenediamine disuccinic acid comprising at least 1.6 mole of alkaline earth metal per mole of ethylenediamine disuccinic acid. Salts of the invention have been found to be useful in providing compositions comprising hydrogen peroxide having improved stability.

7 Claims, 1 Drawing Sheet

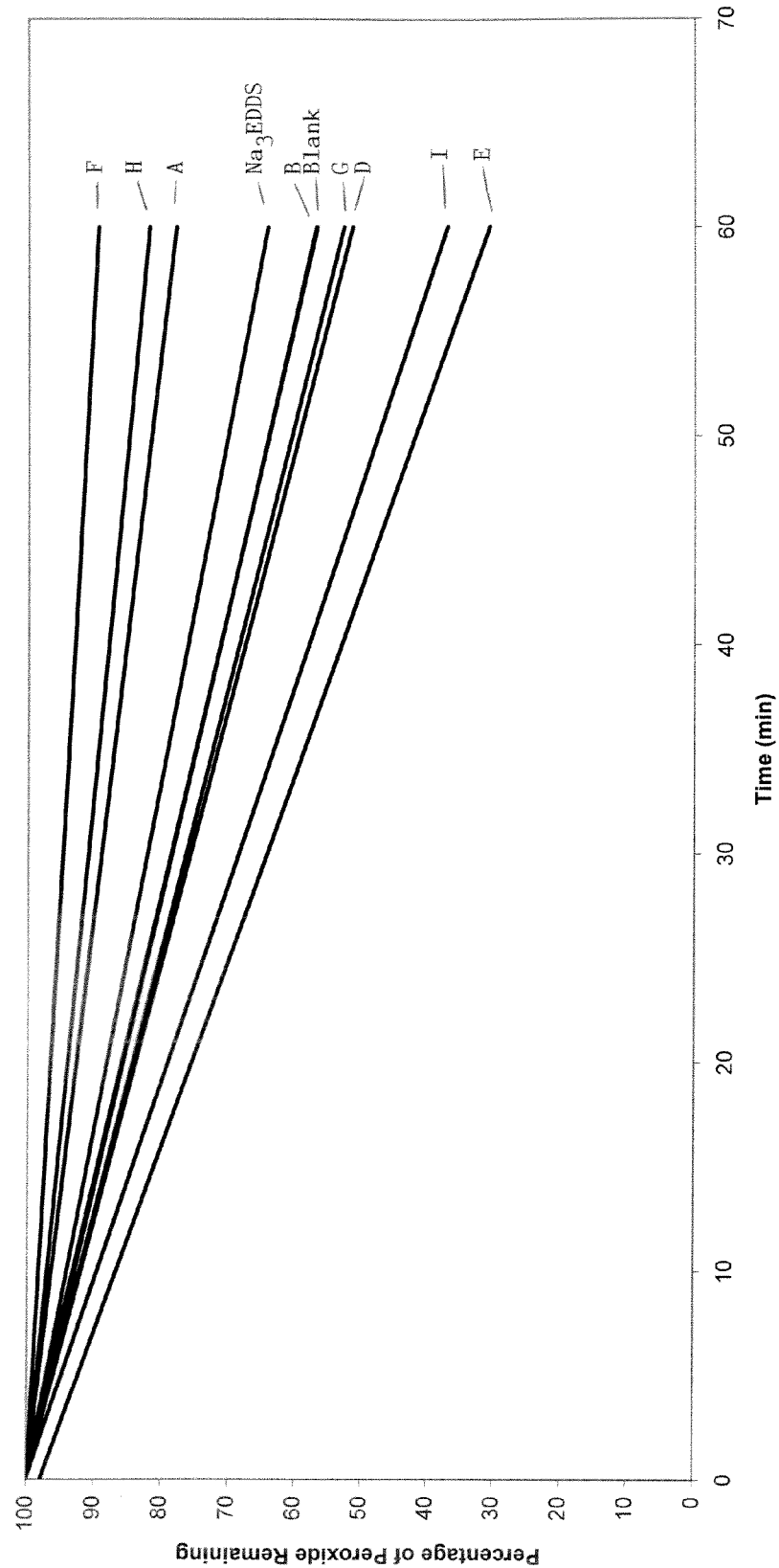

DETERGENT COMPOSITION

CROSS-REFERENCE TO RELATED APPLICATIONS

This application is a U.S. national stage application under 35 U.S.C. 371 of co-pending International Application No. PCT/GB08/50602 filed Jul. 21, 2008 and entitled "COMPOSITION", which in turn claims priority to Great Britain Patent No. 0714575.8 filed Jul. 26, 2007, both of which are incorporated by reference herein in their entirety for all purposes.

The present invention relates to salts of ethylenediamine disuccinic acid (or EDDS). It also relates to methods of preparing such salts, uses thereof and compositions containing said salts. In particular the present invention relates to magnesium-containing salts of EDDS.

Ethylenediamine disuccinic acid has the structure shown in FIG. 1:

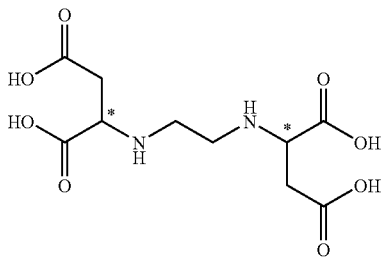

FIG. 1

The structure includes two stereogenic centres and three possible stereoisomers exist. An especially preferred configuration is S,S ethylenediamine disuccinic acid as this compound is readily biodegradable.

Compositions comprising ethylenediamine disuccinic acid and sodium salts thereof are very widely used particularly as chelating agents.

In this specification, the abbreviation "EDDS" is used to denote the structure shown in FIG. 1 and said structure in which a number of the hydroxyl hydrogen atoms have been replaced i.e., "EDDS" may also be used to refer to succinate salts in which 1, 2, 3 or 4 of the acid groups have been neutralised or partially neutralised.

One commercially available material is trisodium ethylenediamine disuccinate. It can be purchased as an aqueous solution comprising 30 wt % EDDS (expressed as free acid) or 37 wt % of trisodium EDDS (including the counterion).

Ethylenediamine disuccinic acid is also commercially available in the form of a solid powder. This contains 65 wt % solid [S,S] EDDS as an acid, and water of crystallisation.

Because EDDS is an effective chelating agent, particularly of heavy metals and transition metals, it is often included in laundry and automatic dishwashing formulations. Such compositions often contain sources of peroxide as a bleaching agent.

EDDS is also used as a chelating agent in pulp and paper bleaching to improve the stability of peroxide bleaching agents. However there exists a continuing need to provide compositions which are more effective at improving the stability of peroxide bleaching agents in these processes.

Such improvements may be beneficial in terms of cost effectiveness and overall performance or may allow lower treat rates to be used to provide equivalent performance.

It is an aim of the present invention to provide a source of EDDS which when included in a composition comprising peroxide leads to improved peroxide stability.

According to a first aspect of the present invention there is provided a salt of ethylenediamine disuccinic acid comprising at least 1.6 mole of an alkaline earth metal per mole of ethylenediamine disuccinic acid.

Preferably the salt comprises at least 1.7 mole of alkaline earth metal per mole of ethylenediamine disuccinic acid, more preferably at least 1.75 mole, for example at least 1.8 mole, preferably at least 1.9 mole, more preferably at least 1.95 mole, and most preferably approximately 2 moles.

Preferably the alkaline earth metal is selected from calcium, magnesium, and mixtures thereof.

Examples of suitable salts include dimagnesium ethylenediamine disuccinic acid, i.e. having 2 moles of magnesium per mole of ethylenediamine disuccinic acid, (a compound in which all 4 hydroxyl hydrogen atoms of FIG. 1 have been replaced by two magnesium ions); dicalcium EDDS having 2 moles of calcium per mole of EDDS; calcium magnesium EDDS having one mole of calcium and one mole of magnesium per mole of ethylenediamine disuccinic acid; and non-stoichiometric equivalents thereof.

The "EDDS" portion of the salt of the present invention may include any of the stereoisomers. Thus it may be selected from [R,R]-EDDS, [R,S]-EDDS, [S,S]-EDDS and any combination thereof.

Preferably the salt comprises at least 50% [S,S]-EDDS, preferably at least 70%, more preferably at least 90%. In some preferred embodiments the salt consists essentially of an alkaline earth metal salt of [S,S]-EDDS.

According to a second aspect of the present invention, there is provided a composition comprising a salt of the first aspect.

The composition may consist essentially of the salt of the first aspect or it may include one or more further components. Preferably the composition further comprises a source of peroxide. Sources of peroxide include hydrogen peroxide, other peroxygen-containing compounds and precursors thereof. For example the composition may comprise a perborate or a percarbonate compound.

A particular advantage of the composition of the present invention is that it improves the stability of hydrogen peroxide in an aqueous solution. In particular, the present invention provides the use of a salt of the first aspect to improve the stability of hydrogen peroxide or other peroxygen-containing compound or precursor thereof in alkaline solution. Compositions of the second aspect comprising a salt of the first aspect and a source of peroxide preferably have a pH of greater than 7.5, for example of between 8 and 14.

Thus the present invention further provides the use of a salt of the first aspect to improve the stability of a composition comprising hydrogen peroxide or other peroxygen-containing compound or precursor thereof.

One way of measuring the stability of a peroxide-containing composition is to measure how the concentration of peroxide falls over time. One such method is described herein in example 2.

Preferably the salt of the present invention stabilises a composition comprising hydrogen peroxide to an extent that at least 65% of the initial hydrogen peroxide remains after a period of one hour, preferably at least 70%, more preferably at least 75%, for example at least 80%.

Suitably when a salt of the present invention is included in a composition comprising hydrogen peroxide, preferably at least 15% additional hydrogen peroxide remains after a period of one hour compared to an equivalent composition in which said salt is absent, more preferably at least 20% additional peroxide remains, preferably at least 25%, suitably at least 30%, for example at least 35% or at least 40% additional peroxide remains.

The inventors have also discovered that the stability of a salt of the first aspect in compositions which comprise hydrogen peroxide or other peroxygen containing compound or precursor thereof is greater than the stability of free tetra acid EDDS or sodium salts of EDDS in a composition comprising hydrogen peroxide or other peroxygen containing compound or precursor thereof.

Thus the present invention further provides a composition comprising a salt of the first aspect and hydrogen peroxide or other peroxygen containing compound or precursor thereof said composition having increased stability compared with a solution having an equivalent amount of trisodium EDDS and hydrogen peroxide or other peroxygen containing compound or precursor thereof.

Preferably when a salt of the present invention is used to replace an equivalent amount of trisodium EDDS in a composition comprising hydrogen peroxide, at least 10% more hydrogen peroxide remains after a period of one hour, for example at least 15% more, preferably at least 20%.

The composition may be a solid composition or a liquid composition. The composition may be of the form of any composition in which trisodium EDDS or ethylenediamine disuccinic acid has previously been incorporated.

The composition may, for example, be a laundry composition or an automatic dishwashing composition. The composition may be in the form of a powder, for example a free flowing powder. Alternatively the composition may be in the form of compressed tablets, or encased, in liquid or solid form, in a shell of a water-soluble polymeric material.

The composition may be a granular composition.

Solid laundry compositions of the present invention preferably comprise from 0.01 to 10 wt %, more preferably 0.01 to 2 wt %, most preferably 0.1 to 0.5 wt % of a salt of the first aspect.

Liquid laundry compositions of the present invention preferably comprise from 0.01 to 25 wt %, more preferably 0.1 to 10 wt %, most preferably 1 to 5 wt % of a salt of the first aspect.

Automatic dishwashing compositions of the present invention preferably comprise 0.1 to 60 wt % of a salt of the first aspect, more preferably 1 to 30 wt % and most preferably 2 to 15 wt %.

Laundry and dishwashing compositions of the present invention preferably comprise further ingredients selected from surfactants, builders, bleaches, bleach activators, redeposition additives, dye transfer inhibitors, enzymes, colorants and fragrances.

The composition of the present invention may be a bleaching composition. It may be a cleaning composition. It may be personal care composition.

In some preferable embodiments, the compositions of the present invention contain from 0.001 to 50 wt %, preferably 1 to 35 wt %, for example 5 to 10 wt % of hydrogen peroxide and from 0.001 to 10 wt %, preferably 0.01 to 1 wt % of the salt of the first aspect. Such compositions are suitably aqueous compositions.

These compositions are particularly useful in paper and pulp bleaching, and may also find utility in laundry and dishwashing applications.

According to a third aspect of the present invention there is provided a method of preparing a salt according to the first aspect.

Preferably the method of the third aspect involves adding a base of an alkaline earth metal to ethylenediamine disuccinic acid. Preferably the method comprises adding a magnesium base to a suspension of ethylenediamine disuccinic acid, preferably an aqueous suspension. Preferably this suspension comprises from 10 to 450, for example 50 to 200 grams of acid per liter of water. Any suitable base can be used. For example, the base may be selected from carbonates, hydroxides, hydrides, amides and oxides. Preferably the base is magnesium hydroxide.

In some embodiments in which the salt comprises a mixed salt, the method of the third aspect may further comprise adding an alkali metal base to ethylenediamine disuccinic acid.

The present invention further provides the use of a salt of the first aspect in any manner in which EDDS-containing materials are used.

As detailed above, the salt of the first aspect is particularly useful in bleaching applications.

The present invention further provides the use of the salt of the first aspect as a chelating agent. In particular the salts of the first aspect of the present invention are used as chelating agents for binding transition metals and heavy metals, for example copper, iron and manganese.

Thus the present invention includes the use of a salt of the first aspect in detergent compositions, for example laundry or automatic dishwashing compositions.

The present invention includes the use of a salt of the first aspect in agricultural applications. For example the salt may be used in slug pellets, in herbicides, in foliar feeds, in nutrient feeds and in hydroponics.

The present invention provides the use of a salt of the first aspect in pulp and paper bleaching. This includes mechanical bleaching and chemical bleaching as well as thermo-mechanical bleaching. The salt of the first aspect may be used in the Q stage and the P stage of the pulp bleaching, that is the wash in which metals are removed and the peroxide stage in which bleaching occurs. These terms are well understood to those skilled in the art.

The present invention provides the use of a salt of the first aspect in personal care applications. For example the salt may be incorporated in hair care compositions, for example hair dyes and shampoo. It may also be included as an antioxidant in creams, for example sun creams and the like.

The present invention includes the use of a salt of the first aspect as a biocide potentiator. As such it may be able to increase the effectiveness of a biocide and may find wide application. For example it may be used in personal care applications.

The present invention provides the use of a salt of the first aspect in household, institutional and industrial cleaning applications. It may be included in hard surface cleaners, bathroom and kitchen cleaners, in bottle washing applications or in the cleaning of dairy equipment.

The present invention further provides the use of a salt of the first aspect as an anti-scalant material, for example as a sequestrant of calcium and magnesium salts.

The salt of the present invention may be used in oil field applications as a scale remover, for example to remove barium and strontium salts.

The present invention may provide the use of a salt of the first aspect in metal cleaning applications, for example printed circuit boards or electroless plating applications.

The present invention may provide the use of a salt of the first aspect in medical applications, for example, as an antipoison material. The present invention may be used to assist the delivery of metals to parts of the body.

Where it is reasonable to do so, any feature of any aspect of the present invention may be combined with any feature of any other aspect. In particular, use of the salt of the first aspect may, where appropriate, include use of a composition of the second aspect.

The invention will now be further described by way of the following non-limiting examples.

BRIEF DESCRIPTION OF THE DRAWING

FIG. 1 is a line graph showing percent of hydrogen peroxide remaining over time.

EXAMPLE 1

Synthesis of Compounds

The products detailed in table 1 were prepared by the following method: In each case, 100.0 g of Enviomet C320 (ethylene diamine disuccinic acid (65% active)) [0.2 moles] was slurried in 1 L de-ionised water and the stated amount of $Mg(OH)_2$ and/or $Ca(OH)_2$ and/or NaOH was added. The mixture was stirred for 17 hours before being filtered. The solution was concentrated and the product was allowed to crystallise out. The white crystalline product was collected by filtration and dried in vacuum oven at 40° C. overnight. The EDDS content was determined by HPLC and the metal content by ICP.

TABLE 1

Preparation and Analysis of Examples

| Example | Mg(OH)₂ Mass (g) | Moles | Ca(OH)₂ Mass (g) | Moles | NaOH Mass (g) | Moles | Analysis: (g/Kg) EDDS | Mg | Ca | Na | Empirical Formula |
|---|---|---|---|---|---|---|---|---|---|---|---|
| A | 25.96 | 0.4 | | | | | 676.1 | 111.0 | | | Mg$_{2.0}$EDDS |
| B (Comparative) | 13.68 | 0.2 | | | | | 694 | 59.3 | | | Mg$_{1.0}$EDDS |
| C (Comparative) | 20.52 | 0.3 | | | | | 730 | 75.2 | | | Mg$_{1.2}$EDDS |
| D (Comparative) | 6.84 | 0.1 | | | 13.31 | 0.3 | 750 | 31.3 | | 81.2 | Na$_{1.4}$Mg$_{0.5}$EDDS |
| E (Comparative) | 13.67 | 0.2 | | | 8.97 | 0.2 | 773 | 54.8 | | 39.8 | Na$_{0.7}$Mg$_{0.9}$EDDS |
| F | 13.67 | 0.2 | 16.29 | 0.2 | | | 654.6 | 45.8 | 70.2 | | Ca$_{0.8}$Mg$_{0.8}$EDDS |
| G (Comparative) | | | 16.29 | 0.2 | 17.60 | 0.4 | 655 | | 127.7 | 36.5 | Ca$_{1.4}$Na$_{0.7}$EDDS |
| H | | | 32.58 | 0.4 | | | 723.1 | | 199.0 | | Ca$_{2.0}$EDDS |
| I (Comparative) | 12.98 | 0.2 | | | 17.81 | 0.4 | 656.7 | 50.8 | | 109.7 | Na$_{2.1}$Mg$_{0.9}$EDDS |

TABLE 2

| Time (min) | 0 | 10 | 20 | 30 | 40 | 50 | 60 |
|---|---|---|---|---|---|---|---|
| Na₃EDDS | 100 | 100 | 90 | 89 | 77 | 65 | 63 |
| A | 100 | 97 | 89 | 89 | 88 | 83 | 76 |
| B (Comparative) | 100 | 92 | 86 | 80 | 73 | 64 | 55 |
| C (Comparative) | 100 | 89 | 80 | 72 | 63 | 57 | 53 |
| D (Comparative) | 100 | 94 | 85 | 77 | 66 | 58 | 52 |
| E (Comparative) | 100 | 90 | 73 | 60 | 49 | 42 | 36 |
| F | 100 | 97 | 96 | 95 | 93 | 91 | 90 |
| G (Comparative) | 100 | 93 | 80 | 71 | 66 | 61 | 58 |
| H | 100 | 97 | 94 | 90 | 88 | 84 | 82 |
| I (Comparative) | 100 | 84 | 79 | 62 | 54 | 49 | 43 |
| Blank | 100 | 92 | 86 | 80 | 73 | 64 | 55 |

EXAMPLE 2

Peroxide Stability

The stability performance of the various salts was compared in a simple peroxide system. In a beaker, 0.1 mmol EDDS compound and water (total volume 125 cm$^3$) were mixed and heated to 40° C. 25 cm$^3$ of a 30% hydrogen peroxide solution was added and the pH adjusted to 10. An aliquot of the solution was taken every 10 minutes and titrated against potassium permanganate. This was used to calculate the concentration of peroxide. The results are shown in table 2. FIG. 1 shows graphical representation of these results in which a line of best fit has been drawn for each set of data. The "blank" sample contained no EDDS compound.

The invention claimed is:

1. A method of improving the stability of a composition comprising hydrogen peroxide or other peroxygen-containing compound or precursor thereof, the method comprising mixing into the composition an amount of a salt of ethylenediamine disuccinic acid comprising at least 1.6 mole of alkaline earth metal per mole of ethylenediamine disuccinic acid; wherein the resulting mixture has increased stability compared with a composition comprising an equivalent amount of a trisodium salt of ethylenediamine disuccinic acid and hydrogen peroxide or other peroxygen containing compound or precursor thereof.

2. The method of claim 1 wherein the resulting mixture is a detergent composition, a personal care composition or a cleaning composition.

3. The method of claim 1 wherein the alkaline earth metal is selected from the group consisting of calcium, magnesium and mixtures thereof.

4. A method of bleaching pulp or paper comprising the steps of:
providing pulp or paper;

contacting the pulp or paper with a composition comprising hydrogen peroxide or other peroxygen-containing compound or precursor thereof; and mixing into the composition an amount of a salt of ethylenediamine disuccinic acid comprising at least 1.6 mole of alkaline earth metal per mole of ethylenediamine disuccinic acid; wherein the resulting mixture has increased stability compared with a composition comprising an equivalent amount of a trisodium salt of ethylenediamine disuccinic acid and hydrogen peroxide or other peroxygen containing compound or precursor thereof.

5. The method according to claim 1, wherein said alkaline earth metal is selected from the group consisting of calcium and mixtures of calcium and magnesium.

6. The method according to claim 4, wherein said alkaline earth metal is selected from the group consisting of calcium and mixtures of calcium and magnesium.

7. A composition of a salt of ethylenediamine disuccinic acid comprising at least 1.6 mole of alkaline earth metal per mole of ethylenediamine disuccinic acid, wherein said alkaline earth metal is selected from the group consisting of calcium and mixtures of calcium and magnesium, and wherein the composition further comprises hydrogen peroxide other than peroxygen containing compounds or a precursor thereof.

* * * * *